US00PP21756P2

(12) United States Plant Patent
Eveleens

(10) Patent No.: US PP21,756 P2
(45) Date of Patent: Mar. 1, 2011

(54) ***GERBERA* PLANT NAMED 'ACADIA'**

(50) Latin Name: *Gerbera jamesonii*
Varietal Denomination: Acadia

(75) Inventor: Jan Leendert Eveleens, Aalsmeer (NL)

(73) Assignee: Florist de Kwakel B.V., Aalsmeer (NL)

( * ) Notice: Subject to any disclaimer, the term of this patent is extended or adjusted under 35 U.S.C. 154(b) by 0 days.

(21) Appl. No.: 12/586,404

(22) Filed: Sep. 21, 2009

(51) Int. Cl.
*A01H 5/00* (2006.01)

(52) U.S. Cl. ..... Plt./357
(58) Field of Classification Search ..... Plt./357
See application file for complete search history.

*Primary Examiner*—June Hwu
*Assistant Examiner*—Louanne C Krawczewicz Myers
(74) *Attorney, Agent, or Firm*—C. A. Whealy

(57) ABSTRACT

A new and distinct cultivar of *Gerbera* plant named 'Acadia', characterized by its compact, upright and uniformly mounding plant habit; freely flowering habit; white-colored ray florets; white-colored disc florets with yellow-colored apices; and upright, strong and relatively short scapes.

1 Drawing Sheet

Botanical designation: *Gerbera jamesonii.*
Cultivar denomination: 'ACADIA'.

BACKGROUND OF THE INVENTION

The present invention relates to a new and distinct cultivar of *Gerbera* plant, botanically known as *Gerbera jamesonii* and hereinafter referred to by the name 'Acadia'.

The new *Gerbera* plant is a product of a planned breeding program conducted by the Inventor in De Kwakel, The Netherlands. The objective of the breeding program is to create new compact container *Gerbera* cultivars with numerous inflorescences, good garden performance and attractive inflorescence coloration.

The new *Gerbera* plant originated from a cross-pollination during the summer of 2005 in De Kwakel, The Netherlands of *Gerbera jamesonii* 'Flocave', disclosed in U.S. Plant Pat. No. 21,339, as the female, or seed, parent with *Gerbera jamesonii* 'Flomite', disclosed in U.S. Plant Pat. No. 21,309, as the male, or pollen, parent. The new *Gerbera* plant was discovered and selected by the Inventor as a single flowering plant within the progeny of the stated cross-pollination in a controlled greenhouse environment in De Kwakel, The Netherlands during the spring of 2006.

Asexual reproduction of the new *Gerbera* plant by tissue culture in a controlled environment in De Kwakel, The Netherlands since the summer of 2006 has shown that the unique features of this new *Gerbera* plant are stable and reproduced true to type in successive generations.

SUMMARY OF THE INVENTION

Plants of the new *Gerbera* have not been observed under all possible environmental conditions. The phenotype may vary somewhat with variations in environment such as temperature and light intensity, without, however, any variance in genotype.

The following traits have been repeatedly observed and are determined to be the unique characteristics of 'Acadia'. These characteristics in combination distinguish 'Acadia' as a new and distinct cultivar of *Gerbera:*

1. Compact, upright and uniformly mounding plant habit.
2. Freely flowering habit.

3. White-colored ray florets.
4. White-colored disc florets with yellow-colored apices.
5. Upright, strong and relatively short scapes.

Plants of the new *Gerbera* differ from plants of the female parent, 'Flocave', in the following characteristics:

1. Plants of the new *Gerbera* have stronger leaves than plants of 'Flocave'.
2. Plants of the new *Gerbera* have shorter scapes than plants of 'Flocave'.
3. Plants of the new *Gerbera* have more uniform inflorescences than plants of 'Flocave'.
4. Inflorescences of plants of the new *Gerbera* have longer and more numerous inner ray florets than inflorescences of plants of 'Flocave'.
5. Disc florets of plants of the new *Gerbera* have yellow-colored apices whereas disc florets of plants of 'Flocave' have pink-colored apices.

Plants of the new *Gerbera* differ from plants of the male parent, 'Flomite', primarily in ray floret color as plants of 'Flomite' have orange red-colored ray florets.

Plants of the new *Gerbera* can be compared to plants of the *Gerbera jamesonii* 'Everlast White', not patented. Plants of the new *Gerbera* differ from plants of 'Everlast White' in the following characteristics:

1. Plants of the new *Gerbera* are more uniform in growth habit than plants of 'Everlast White'.
2. Plants of the new *Gerbera* have larger inflorescences than plants of 'Everlast White'.
3. Plants of the new *Gerbera* have semi-double type inflorescences whereas plants of 'Everlast White' have single type inflorescences.
4. Plants of the new *Gerbera* have thicker scapes than plants of 'Everlast White'.

BRIEF DESCRIPTION OF THE PHOTOGRAPH

The accompanying photograph illustrates the overall appearance of the new *Gerbera* plant. The photograph shows the colors as true as it is reasonably possible to obtain in colored reproductions of this type. Colors in the photograph may differ slightly from the color values cited in the detailed botanical description which accurately describe the colors of the new *Gerbera* plant. The photograph comprises a side perspective view of a typical flowering plant of 'Acadia' grown in a container.

DETAILED BOTANICAL DESCRIPTION

The aforementioned photograph and following observations and measurements describe plants grown in a glass-covered greenhouse during the spring and summer in De Kwakel, The Netherlands and under conditions and practices which approximate those generally used in commercial container *Gerbera* production. During the production of the plants, day temperatures ranged from 19° C. to 26° C. and night temperatures ranged from 16° C. to 18° C. Rooted young tissue-cultured plants were planted in 19-cm containers and were six months old when the photograph was taken and ten months old when the description was taken. In the following description, color references are made to The Royal Horticultural Society Colour Chart, Fifth Edition, 2007, except where general terms of ordinary dictionary significance are used.

Botanical classification: *Gerbera jamesonii* 'Acadia'.

Parentage:

*Female, or seed, parent.*—*Gerbera jamesonii* 'Flocave', disclosed in U.S. Plant Pat. No. 21,339.

*Male, or pollen, parent.*—*Gerbera jamesonii* 'Flomite', disclosed in U.S. Plant Pat. No. 21,309.

Propagation:

*Type.*—By tissue culture.

*Time to initiate roots.*—About 2.5 weeks at temperatures of 20° C.

*Time to produce a rooted young plant.*—About five to six weeks at temperatures of 20° C. to 26° C.

*Root description.*—Fibrous; white in color.

*Rooting habit.*—Moderate branching; dense.

Plant description:

*Appearance.*—Herbaceous perennials with semi-double inflorescences that are typically grown as a container or garden plants; compact, upright and uniformly mounding plant habit; leaves arranged in basal rosettes and outwardly arching; dense and bushy habit; moderately vigorous growth habit.

*Plant height.*—About 49 cm.

*Plant width.*—About 70 cm.

Foliage description:

*Arrangement.*—Alternate, simple.

*Length.*—About 47 cm.

*Width.*—About 14 cm.

*Shape.*—Runcinate; lanceolate to narrowly elliptic in outline.

*Apex.*—Obtuse to abruptly acute.

*Base.*—Acuminate.

*Margin.*—Pinnately lobed with coarse and irregular sinuses, lobes divergent; undulate.

*Texture, upper surface.*—Sparsely pubescent.

*Texture, lower surface.*—Moderately pubescent; woolly.

*Venation pattern.*—Pinnate.

*Color.*—Developing leaves, upper surface: Close to 139A. Developing leaves, lower surface: Close to 137C. Fully expanded leaves, upper surface: Close to N139A; venation, close to 144B. Fully expanded leaves, lower surface: Close to 137C; venation, close to 144B.

*Petioles.*—Length: About 12 cm. Diameter: About 6 mm. Texture, upper surface: Sparsely pubescent. Texture, lower surface: Moderately pubescent. Color, upper and lower surfaces: Close to 143B.

Inflorescence description:

*Appearance.*—Semi-double type inflorescence form with narrowly obovate-shaped ray florets; solitary inflorescences borne on upright, strong and relatively short scapes above the foliar plane; ray and disc florets arranged acropetally on a capitulum.

*Fragrance.*—None detected.

*Flowering season.*—Plants begin flowering about four months after planting and flower from early spring to the end of the summer in outdoor gardens in The Netherlands; plants flower year-round under greenhouse conditions.

*Inflorescence longevity.*—Inflorescences last about two weeks on the plant; inflorescences persistent.

*Quantity of inflorescences.*—Freely flowering habit with about eight open and developing inflorescences per plant at one time.

*Inflorescence bud.*—Height: About 1.6 cm. Diameter: About 3.6 cm. Shape: Oblate. Color: Close to 144B; mid-section, close to 203D.

*Inflorescence size.*—Diameter: About 10.5 cm. Depth (height): About 2.5 cm. Diameter of disc: About 3 cm. Receptacle height: About 9 mm. Receptacle diameter: About 9 mm. Receptacle color: Close to NN155C.

*Ray florets.*—Orientation: Initially upright, then roughly perpendicular to the peduncle and reflexing. Length: About 5.2 cm. Width: About 1.1 cm. Shape: Narrowly obovate. Apex: Obtuse, rounded. Base: Cuneate. Margin: Entire. Texture, upper and lower surfaces: Smooth, glabrous; longitudinally ridged. Number of ray florets per inflorescence: About 95 outer ray florets and about 600 inner ray florets arranged in about four whorls. Color: When opening, upper surface: Close to NN155A to NN155B. When opening, lower surface: Close to 150D; towards the base, close to 157D. Fully opened, upper surface: Close to NN155D. Fully opened, lower surface: Close to 150D.

*Disc florets.*—Arrangement: Massed at center of receptacle. Shape: Tubular, fused. Apex: Acute. Base: Fused. Margin: Entire. Length: About 1 cm. Width: About 4.5 mm. Texture, upper and lower surfaces: Smooth, glabrous. Number of disc florets per inflorescence: About 500. Color, immature: Close to 202A. Color, mature: Apex, close to 6D; mid-section and base, close to N155A to 155A.

*Pappus.*—Quantity per floret: About 50. Length: About 8 mm. Diameter: Less than 1 mm. Texture: Soft. Color: Close to N77A and 187A.

*Phyllaries.*—Number of phyllaries per inflorescence: About 100 in about three to four whorls. Length: About 1.5 cm. Width: About 3.1 mm. Shape: Lanceolate. Apex: Acute. Base: Cuneate. Margin: Entire. Texture, upper surface: Smooth, glabrous. Texture, lower surface: Densely tomentose. Color, upper surface: Close to 143A. Color, lower surface: Close to 137B.

*Scapes.*—Length: About 40 cm. Diameter: About 8 mm. Angle: Erect. Strength: Strong. Texture: Densely tomentose. Color: Close to 144B; towards the apex, close to 137B.

*Reproductive organs.*—Androecium: Present on disc florets only. Quantity per floret: Two. Filament length: About 6 mm. Filament color: Close to NN155C. Anther shape: Lanceolate. Anther length: About 4 mm. Anther color: Close to 12B. Pollen amount: Moderate. Pollen color: Close to 12A. Gynoecium: Present on disc and ray florets. Quantity per floret: One. Pistil length: About 1.1 cm. Stigma shape: Rounded; curved. Stigma color: Close to 155D. Style length: About 1 cm. Style color: Close to NN155C. Ovary color: Close to 145D.

*Seed/fruit.*—Seed and fruit production has not been observed.

Disease/pest resistance: Resistance to pathogens and pests common to *Gerberas* has not been observed on plants of the new *Gerbera* grown under commercial conditions.

Temperature tolerance: Plants of the new *Gerbera* have been observed to tolerate temperatures from about 1° C. to about 35° C.

It is claimed:

1. A new and distinct *Gerbera* plant named 'Acadia' as illustrated and described.

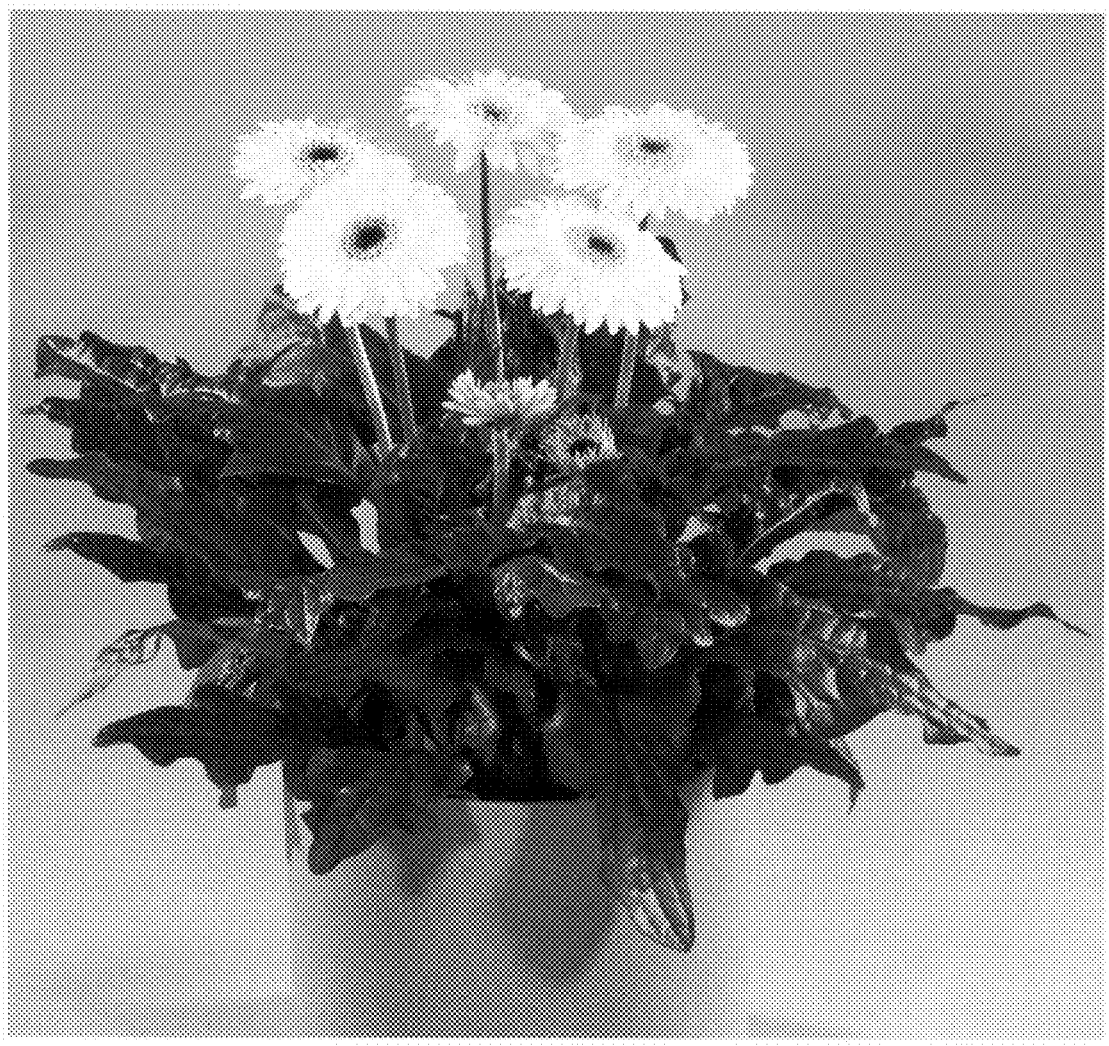

* * * * *